United States Patent
Breitschmid

Patent Number: 5,394,584
Date of Patent: Mar. 7, 1995

[54] RETAINING MEMBER ON A HANDLE, AND DENTAL BRUSH FOR EXCHANGEABLE ATTACHMENT TO A HOLDER

[75] Inventor: Ueli Breitschmid, Meggen, Switzerland

[73] Assignee: Breitschmid AG., Kriens, Switzerland

[21] Appl. No.: 989,657

[22] Filed: Dec. 14, 1992

[30] Foreign Application Priority Data

Jan. 9, 1992 [CH] Switzerland ............... 049/92

[51] Int. Cl.⁶ .................................. A46B 3/08
[52] U.S. Cl. ......................... 15/167.1; 15/145; 15/176.5; 15/176.6
[58] Field of Search ........... 15/167.1, 143.1, 145, 15/176.1, 176.4, 176.5, 176.6; 433/147, 146, 142, 127, 128

[56] References Cited

U.S. PATENT DOCUMENTS

| | | | |
|---|---|---|---|
| 1,908,510 | 5/1933 | Dodson | 15/176.4 |
| 3,204,275 | 9/1965 | Baker | 15/167.1 |
| 4,319,377 | 3/1982 | Tarrson et al. | 15/145 |
| 4,370,773 | 2/1983 | Hadary | 15/176.4 |
| 4,387,479 | 6/1983 | Kigyos | 15/167.1 |
| 4,534,081 | 8/1985 | Spademan | 15/167.1 |
| 4,543,679 | 10/1985 | Rosofsky et al. | 15/176.4 |
| 4,751,761 | 6/1988 | Breitschmid | 15/176.5 |
| 4,805,252 | 2/1989 | Tarrson et al. | 15/176.1 |
| 5,144,712 | 9/1992 | Hansel et al. | 15/176.6 |

FOREIGN PATENT DOCUMENTS

| | | |
|---|---|---|
| 0001044 | 3/1979 | European Pat. Off. . |
| 0203082 | 4/1989 | European Pat. Off. . |
| 413683 | 8/1910 | France ........ 15/176.1 |
| 294895 | 12/1928 | United Kingdom ........ 15/176.1 |
| WO86/02532 | 5/1986 | WIPO . |

Primary Examiner—David A. Scherbel
Assistant Examiner—Tony G. Soohoo
Attorney, Agent, or Firm—Brady, O'Boyle & Gates

[57] ABSTRACT

A retaining member on a handle for the exchangeable attachment of an interdental brush (29) exhibiting a fastening element (36) with transverse element (37) has a recess which is designed so that the interdental brush (29) can be introduced in the direction of its longitudinal axis, with the transverse element (37) leading, into the recess (34) and can be locked in place in the latter especially by being folded over.

8 Claims, 3 Drawing Sheets

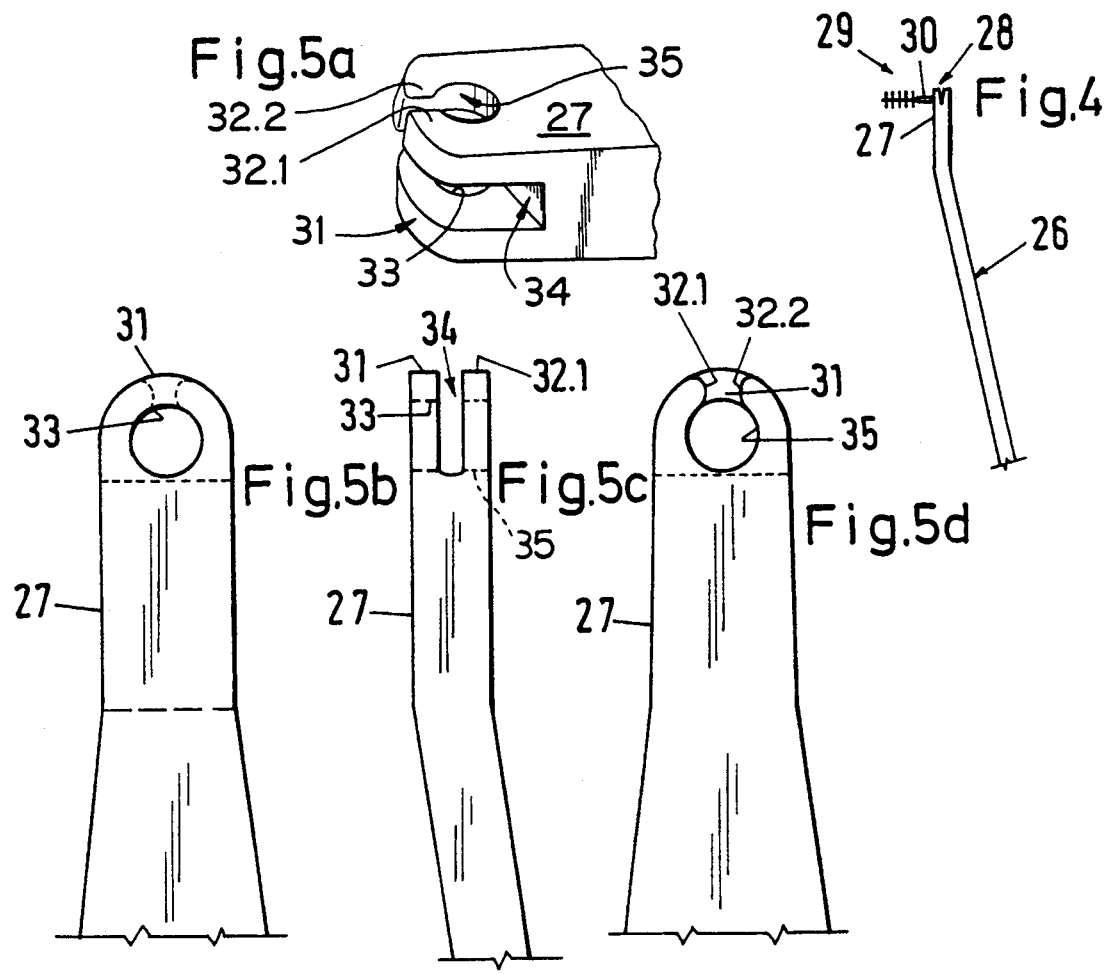
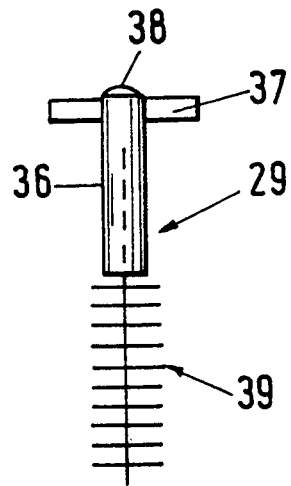
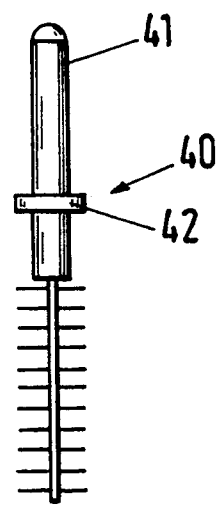

RETAINING MEMBER ON A HANDLE, AND DENTAL BRUSH FOR EXCHANGEABLE ATTACHMENT TO A HOLDER

FIELD OF ART

The invention relates to a retaining member on a handle for the exchangeable attachment of an interdental brush exhibiting a fastening element with crosspiece by inserting the fastening element in a recess of the retaining member. The invention furthermore concerns a dental brush for the exchangeable mounting to a holder, comprising a bristle-studded frontal section and a rear end provided with a fastening means.

STATE OF THE ART

EP-A-001,044 discloses a tooth cleaning device wherein an interdental brush is exchangeably attachable to a handle. The interdental brush has a cylindrical clamping plug insertable with a clamping fit in a blind hole of the handle. However, if the interdental brush seizes in a tooth interspace and consequently the user attempts to pull the interdental brush out of the tooth interspace by strongly tugging at the handle, the clamping plug with be detached from the clamping seat. Thus, the user must seize the molded piece by putting his hand in his mouth, and this is troublesome on account of the small size of this piece.

A dental brush of the type discussed hereinabove has been known from WO-86/025 32, avoiding this problem. The brush is retained in exchangeable fashion at one end of a handle. The handle end has a bolt thread on which a threaded sleeve is seated; a through hole which extends transversely through the bolt thread; and a longitudinal groove. The bristle carrier of the brush is mounted in a cylindrical fitting of a synthetic resin, a traverse being formed at the free end thereof and constituting an abutment. The brush is pushed with the bristles pointing forward through the passage hole. The traverse is introduced into the groove, and the threaded sleeve is threaded on the screw thread over the traverse so that the latter is fixedly clamped between the sleeve and the bottom of the groove.

This type of fastening, though very rugged and obviating a breaking off of the bristle carrier at its attachment, does require a backward and forward threading of the threaded sleeve each time the dental brush is exchanged.

DESCRIPTION OF THE INVENTION

It is an object of the invention to provide a retaining member of the above-mentioned type to which an interdental brush can be attached in a simple, quick and reliable fashion.

According to the invention, this object has been attained by designing the recess in such a way that the interdental brush can be introduced into the recess in the direction of the longitudinal axis of the brush with the crosspiece leading, and can be locked in place in this recess.

Accordingly, one manipulation suffices, in principle, for mounting the brush. The crosspiece formed at the fastening element of the brush ensures that the connection can be subjected to high tensile stress. Differently from the state of the art, the crosspiece, in this invention, is introduced into the recess and can lock in place therein.

In accordance with an especially preferred embodiment, the recess is designed so that, after the axial introduction of the fastening element, the locking action can be brought about by folding the interdental brush over about an axis perpendicular to the longitudinal axis. The crosspiece in this case is preferably a traverse provided at a small distance to the rear end of the fastening element. The interdental brush is foled about this traverse for obtaining the locking engagement.

The recess comprises advantageously a slot-shaped zone for receiving a longitudinal element of the fastening element, formed by a pincer-like section. The longitudinal section is introduced into the pincer-like section by folding over. The crosspiece prevents the mounted interdental brush from being pulled through between the pincerlike member in the axial direction. For purposes of exchange, the brush must in any event first be folded back. The pincer-like section is fashioned so that the longitudinal section locks in place in the fastening position. A locking action achieved solely by the crosspiece is likewise possible.

If the crosspiece is a traverse, then the recess typically includes a T-shaped slot arrangement with longitudinal slot and transverse slot. The fastening element is first introduced into the transverse slot with the traverse leading and is then folded over so that the longitudinal element comes to lie in the longitudinal slot. The T- or cross-shaped slot arrangement can also be designed so that folding over of the interdental brush is not necessary, but rather the fastening element is introduced perpendicularly to its longitudinal axis.

According to a preferred embodiment, a cavity is formed on one side of the transverse slot, oppositely to the longitudinal slot, this cavity subtending the slot opening. The rear end of the fastening element is placed in this cavity. This protects the longitudinal element from being pushed out of the recess perpendicularly to the axis of the element.

In accordance with an especially preferred embodiment, the recess is designed at the same time for the force-locking attachment of an insertable interdental brush. The aforementioned cavity can be designed, for example, as a hole wherein the aforementioned insertable interdental brush can be mounted in forcelocking fashion.

The invention is distinguished in that no movable parts are required for constructing the invention. The retaining member as such is, therefore, preferably made of one piece. The handle and the retaining member can be made, for example, as a plastic injection-molded part. In contrast thereto, a longlife, high-quality tooth cleaning device is produced preferably from a metal. In this arrangement, the design of the retaining member according to this invention can be produced by simple means (drilling, milling).

Conventional dental brushes, but also novel ones, can be mounted to the retaining member of this invention. Quite generally, the dental brushes usable in the present invention have a bristle-studded forward section and a rear end equipped with a fastening means. The fastening means is typically a molded part.

A special dental brush within the scope of the invention is distinguished in that the fastening means is fashioned so that it constitutes one part of a closure of a snap fastener type. Consequently, the connection is established by axial locking action.

In order to ensure an elastic movability and, respectively, a flexible guidance of the bristle-studded section, the part designed as the fastening means can exhibit a resilient annular shoulder to be supported on the holder.

Advantageously, the part designed as a fastening means is the rearward section of a bridge arranged behind the bristle-studded forward section of the dental brush.

Preferably, the part designed as the fastending means has a recess with a narrowed opening. The corresponding other part of the snap-fastener closure is provided on a holder for the exchangeable mounting of the dental brush. Preferably, the other part, formed at the holder, is designed as a projecting element with a constriction.

In principle, the situation could also be reversed, the projecting element being arranged at the dental brush.

Since the projecting element is under great stress, it is preferably made of a hard, rugged material, such as, for example, plastic or, preferably, metal. In view of the fact that the dental brush is destined for one-time use, it is advantageous to make same in a maximally inexpensive way, and without metallic formed parts. The bridge is preferably made of a soft-elastic material.

The part of the snap-fastener closure formed at the rear end of the dental brush can, however, consist just as well of an inelastic plastic (or some other hard material). In order to improve the snap action in such closure parts, the projecting element can be split along its longitudinal axis once or in the manner of a cross. The thus-formed "individual parts" of the projecting element consequently are elastically supported transversely to the longitudinal axis to a minimum but adequate extent. When the two corresponding parts of the closure are joined, they are slightly pressed together and spring back toward the outside during the locking step (in the radial direction).

In accordance with an especially preferred embodiment, the recess has at least in an approximation a spherical shape so that a ball-and-socket joint mobility of the closure is made possible. The resilient annular shoulder exerts a force which aligns the forward section when resting on the holder. Normally, in dental brushes according to this invention, the bristles are retained between twisted wires. The bristle carrier formed in this way is relatively rigid. In view of this, it is advantageous to provide a transition that is movable in ball-and-socket joint fashion between the handle and the bristle carrier.

The transition bridge is advantageously fashioned in the manner of a stimulator. For this purpose, it is of a shape Which conically converges toward the bristle-studded section. The transition piece can have essentially a conical shape, the apex of the cone facing the bristle-carrying section and the recess being formed in the base with a narrowed opening.

An especially good stimulating effect results if axial longitudinal ribs of a soft-elastic material are provided at the conical or, respectively, cone-shaped transition piece.

According to this invention, a whole set of differing dental brushes can be provided for the handle. Although all of them have the same snap-fastener closure at the rear end, they differ, for example, with respect to the length of the bristles or the type of bridge piece. (One set along these lines can encompass varying dental brushes with stimulators and/or of different colors.)

Additional preferred embodiments of the invention can be derived from the entirety of the claims and the following description.

BRIEF DESCRIPTION OF THE DRAWINGS

The invention will be described in greater detail below with reference to embodiments and in conjunction with the drawings wherein:

FIG. 4 shows a handle with interdental brush attached thereto;

FIGS. 5a–d show schematical views of a retaining member in a top view (FIG. 5a) and in three lateral views (FIGS. 5b–d);

FIG. 6 shows an interdental brush with traverse;

FIG. 7 shows a pluggable interdental brush;

Basically, corresponding parts in all figures bear identical reference numerals.

POSSIBILITIES OF EXECUTING THE INVENTION

Figure 1:
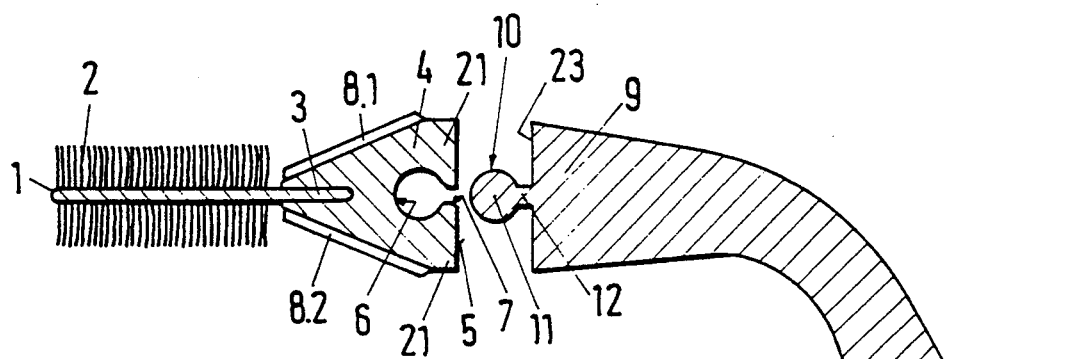
FIG. 1 shows a dental brush with a spherical fastening element designed as a ball-and-socket joint.

FIG. 1 shows, in a sectional view, a dental brush and a handle with a corresponding holder for the dental brush. The dental brush comprises a forward section designed in the manner of a small circular brush. The bristles 2 are conventionally retained between two mutually twisted sections of a wire 1. The twisted wire 1 has a rear end 3 retained by a transition piece 4. The bridge 4 is preferably made of a soft-elastic material (plasticized synthetic resin, rubber, etc.). The transition piece has a conical shape, the rear end 3 being inserted in the apex of the cone. In the base 5 of the conical transition piece 4, a preferably spherical recess 6 having a constricted opening 7 is formed. A number of (for example, a dozen) longitudinal ribs 8.1, 8.2 is located on the surface of the conical shell, two of these ribs being shown schematically in the figure. They are suitable for stimulating the papillae by exertion of pressure.

The dental brush can be exchangeably fastened to a holder 9. In accordance with the invention, the fastening means are designed along the lines of a snap-fastener connection. One part (recess 6, narrowed opening 7) of this connection has been explained above. The other one is embodied by a projecting element 10. The projecting element 10 corresponds in its shape essentially to the complement of the recess 6 with the constricted opening 7.

In the present case, the projecting element 10 is a spherical entity with a neck. In the generalized form, the head represents a broadened section 11 (crosspiece) and the neck a constriction 12 (longitudinal element). The projecting element 10 preferably molded to the holder 9 thus has the configuration of a mushroom.

In order to fasten the dental brush to the holder 9 and thus to the associated handle 13, the transition piece 4 must be pushed with the narrowed opening 7 over the broadened section 11. On account of the constriction 12 provided behind the broadened portion 11, a snap effect is achieved. The recess 6 and the broadened section 11 are advantageously adapted to each other in such a way that a press fit is obtained in the joined condition. The fitting can, however, also be chosen so that, upon the exertion of a force, the transition element 4 is displaceable on the head of the projecting element.

Due to the spherical configuration of the recess 6 and the broadened portion 7, a movability along the lines of a ball-and-socket joint is furthermore imparted to the closure. The transition piece 4 is, after all, made of an elastic material. If, now, the wire 1 is exposed to a force transversely to its longitudinal axis, this force is transmitted to the transition piece 4. A portion of this force is absorbed by the transition piece proper on account of its conicity, and the other portion is absorbed by the closure due to the ball-and-socket joint design of the elements. The longitudinal ribs 8.1 and 8.2 can additionally deploy a stabilizing effect during this step. In other words, they reinforce the conical part of the transition piece 4 so that a larger part of the transverse force acting on the wire 1 is conducted to the ball-and-socket joint-like snap-fastener closure. The outer rim of the base of the conical transition piece is constituted by a resilient annular shoulder 21. The latter rests on the holder, in particular on the surface 23 surrounding the projecting element. Under the spring action of the annular shoulder 21, the wire 1 is retained laterally elastically in a rest position. During cleaning of the teeth in the interdental spaces, the wire 1 can thus find its way around the teeth on account of the flexible support.

A vigorous tug on the end carrying the bristles is sufficient for removing the dental brush. Alternatively, the dental brush can be released from the holder 9 by a strong lateral pressure exerted on its forward part.

Figure 2:
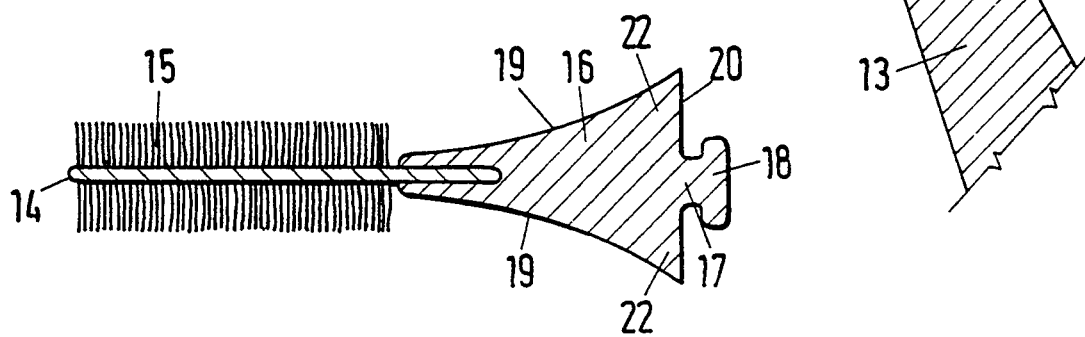
FIG. 2 shows a dental brush with a concave-conical surface.

FIG. 2 shows another preferred embodiment of the invention. Here, too, the dental brush comprises a forward, bristle-studded section (wire 14 and bristles 15) and a transition piece 16. In contrast to the first embodiment, the transition piece 16 here has a conically concave outer surface 19. Thereby, the movability in ball-and-socket joint fashion can be increased. The spring effect here again is substantially brought about by the marginal zones of the base 20 of the conically concave transition piece 16 along the lines of a preferred annular shoulder 22.

Another difference with respect to the first embodiment resides in that the projecting part of the biparrite, snap-fastener closure is formed at the transition piece 16 rather than at the holder. The projecting element is designed, for example, in the manner of two short cylinders stacked, so to speak, one upon the other. The first of these two cylinders, resting directly on the base of the conical transition piece 16, has a smaller diameter than the second, subsequent cylinder. The first cylinder thus embodies the constriction 17 and the second cylinder constitutes the broadened section 18 or the crosspiece. Thus, an annular recess is formed between the base 20 of the transition piece 16 and the broadened section 18; a corresponding molded part of a holder (not shown in FIG. 2) can engage into this recess.

The snap effect during joining of the closure according to FIG. 2 is preferably produced by the feature that the transition piece 16 consists of a soft-elastic synthetic resin which can be compressed upon the insertion of the projecting part (constriction 17, broadened portion 18) in a metallic holder. Alternatively, it is, of course, also possible for the transition piece 16 to consist of an inelastic material, and the holder to consist of an elastic material.

It is just as readily possible to make both parts of the closure of relatively inelastic materials; in this case, the snap effect can be attained by an additional, resilient mechanism at the holder.

Figure 3:
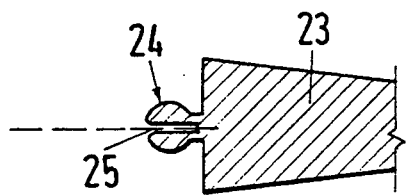
FIG. 3 shows a slotted, projecting element in a cross-sectional view.

FIG. 3 shows a further possibility for realizing the snap closure in case of inelastic materials. In FIG. 3, the forward end of a holder 9 is shown exhibiting a projecting element 24. The latter, in accordance with a preferred embodiment, is slotted along its longitudinal axis (slot 25). The slot arrangement will typically be a single slot or a cross-like pattern. The "branches" produced my the slotting (2 or 4) can be slightly but adequately compressed in the radial direction even if the holder 9 and the projecting element 24 consist of an inelastic material.

Dental brushes according to FIG. 1 can be readily placed onto the projecting element 24 (in case the transition piece 4 is made of an elastic material, as well as in case it consists of a hard material).

By a combination of the individual features of the aforedescribed embodiments, additional advantageous devices for cleaning interdental spaces are created.

Basically, all embodiments can be designed with or without longitudinal ribs. If the transition piece is made of a soft-elastic material, then a stimulating action can also be achieved during tooth cleaning even without these ribs.

The projecting element of the bipartite closure of the snap fastener type can be molded to the holder or just as well also to the transition piece. The advantages that can be realized in each case depend, for example, on the type of materials utilized and on the structure of the holder.

A large number of variation possibilities exist for the shape of the parts that can be placed in locking engagement in the manner of a snap fastener. Only two of these are illustrated by way of example in the figures. In the embodiment illustrated in FIG. 2, wherein the projecting element has a T-shaped cross section, the ball-and-socket joint-like mobility will probably be extensively absent.

In FIG. 1, the holder 9 and the handle 13 form a single element that cannot be varied in its shape. Such a handle can be manufactured in an especially advantageous fashion. However, it is definitely also possible to use sophisticated handles with adjustable angle.

The snap-fastener closure can furthermore also be utilized in electric toothbrushes or other devices of dental hygiene, wherein the interdental brush is shaken, vibrated, or rotated by a motor.

The snap-fastener closure need not be designed to be rotationally symmetrical. In analogy to FIG. 2, two square members of differing sizes can serve for the formation of the projecting element, in place of two short cylinderical members. It is understood, in this connection, that, in reality, the projecting element is preferably formed as one piece, i.e. as a molded-on part, rather than as two separate, assembled pieces.

One embodiment with a retaining member according to this invention will be described below:

FIG. 4 shows a handle 26 with an angled end 27 at which a retaining member 28 is formed. In accordance with an especially preferred embodiment, the handle 26, the angled end 27, and the retaining member 28 are a single molded part (for example a plastic injection-molded part). An interdental brush 29 is exchangeably retained at its fastening element 30 in the retaining member 28. As will be described further below, the fastening element 30 is likewise a molded part of a synthetic resin.

FIGS. 5a–d show the angled end 27 with the retaining member 28 in an enlarged view and from different viewing directions. The handle 26 and the angled end 27 are typically flat and of rectangular cross section. An annular part 31 and two fingers 32.1, 32.2 act as the bifurcated cad retaining member protruding or cantilevered in the longitudinal direction of the handle from end of the handle. The annular part 31 has a hole 33. A transverse slot 34 is formed between the annular part 31 and the two fingers 32.1, 32.2. The two fingers 32.1, 32.2 cantilevered in the longitudinal direction of the handle, constitute a pincer-like member with longitudinal slot 35. As can be seen from FIG. 5a, the longitudinal and transverse slots (35 and 34) form a T-shaped slot arrangement.

The hole 33 is arranged in alignment with the longitudinal slot 35 and forms a cavity subtending the T-slot arrangement on a sidewall of the transverse slot 34 lying in opposition to the longitudinal slot 35.

Interdental brushes of differing designs can be attached in the retaining member according to FIGS. 5a–d.

FIG. 6 shows an interdental brush 29 with a longitudinal element 36 and a traverse 37 (crosspiece). The traverse 37 is arranged in the proximity of the rear end 38 of the longitudinal element 36. The rear end 38 thus projects slightly beyond the traverse 37. The wire retaining the bristles 39 is molded into the longitudinal element 36.

FIG. 7 shows an insertable interdental brush 40. A longitudinal element 41 is designed preferably in the manner of a cylindrical plug. It has an annular shoulder 42 typically molded to the longitudinal element 41 in the forward half of the latter.

Figure 8A:
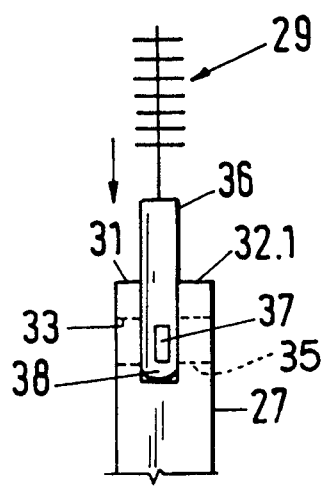
FIGS. 8a,b show schematic views of the two steps for fastening an interdental brush by folding over.

The manner of fastening the interdental brush 29 in the retaining member will now be described with reference to FIGS. 8a, 8b. This is done, in principle, in two partial steps. First of all, the interdental brush 29 is inserted, with the traverse 37 leading, in the longitudinal direction with respect to the longitudinal element 36, from above in the cross notch 34 (compare arrow in FIG. 8a). As the second step, the interdental brush 29 is folded over by 90°. The traverse 37 here represents the axis of rotation. By the folding step, the longitudinal element 36 is pushed between the pincer-like fingers 32.1, 32.2 (i.e. into the longitudinal slot 35).

The traverse 37 is of rectangular cross section in accordance with a preferred embodiment. The rectangular profile is here larger in the direction of the longitudinal axis of the longitudinal element 36 than perpendicularly thereto. The aforementioned length is, in particular, precisely about the same size as the width of the transverse slot 34. As can be seen from FIG. 8b, this results in a satisfactory fixation of the interdental brush in the mounted position (traverse 37 is fixedly clamped between the annular section 31 and the two fingers 32.1, 32.2).

Figure 8B:
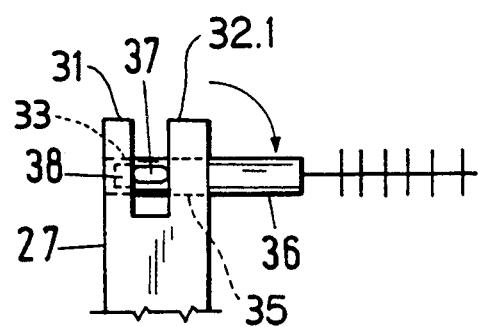

As can furthermore be seen from FIG. 8b, the projecting end 38 of the fastening element extends into the hole 33. The diameter of the longitudinal element 36 is adapted to the internal diameter of the hole 33 in such a way that the longitudinal element 36 is firmly seated not only between the fingers 32.1, 32.2, but also in the annular part 31.

Due to the feature that the two fingers 32.1, 32.2 have a pincer-like structure, the longitudinal element 36 can lock in place in the mounted position.

Figure 9:
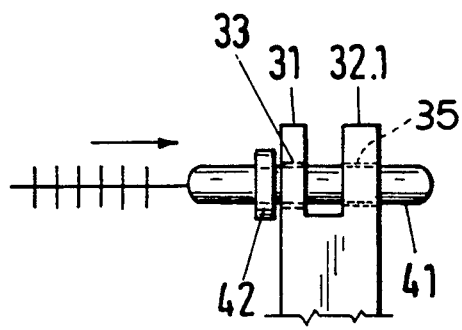
FIG. 9 illustrates an interdental brush retained in the retaining member by force-locking connection.
Figure 10:
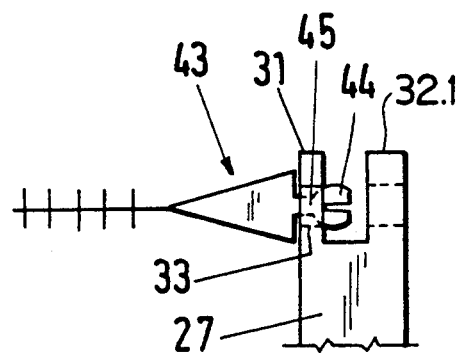
FIG. 10 shows an interdental brush retained in the retaining member along the lines of a snap-fastener mounting.

FIG. 9 shows how the pluggable interdental brush 40 according to FIG. 7 is to be mounted in the retaining member. The brush is inserted, with its plug-like longitudinal element 41, in the hole 33 of the ring-shaped part 31 until the annular shoulder 42 is in contact with the ring-shaped part 31. The longitudinal element 41 is of such a length that it is likewise clamped in place by the fingers 32.1, 32.2 (in the longitudinal slot 35). The size of the hole 33 is adapted to the longitudinal element 41 with a view toward satisfactory force-locking connection.

The insertable interdental brush 40 can, of course, also be introduced from the other side, i.e. first of all between the two fingers 32.1, 32.2 and only then through the hole 33.

In the retaining member according to FIGS. 5a–d, a dental brush 43 can also be mounted comprising a snap-fastener-like connecting element, as illustrated in FIG. 3. The compressible head 44 which is slotted, for example, is urged through the hole 33 of the annular part 31 and locks in place therein. The neck 45 is thus encompassed by the annular part 31.

An interdental brush with a projecting element according to FIG. 2 can also be fixed in place by the introduction of the constriction 17 between the fingers 32.1, 32.2, the broadened portion 18 coming to lie in the transverse slot 34. The interdental brush is thus introduced transversely to its longitudinal axis into the longitudinal slot 35. In case the constriction 17 is somewhat wider than the narrowed slot-shaped opening of the longitudinal slot, it can be placed in locking fashion into the mounted position while overcoming a certain resistance.

The retaining member, described by way of example with reference to the figures, can be modified in various ways. Thus, for example, the annular part 31 can be replaced by a pincer-like member (corresponding to the fingers 32.1, 32.2). In place of the annular section 31, a solid rear wall (without a hole 33) can also be provided, in principle.

The recess can also be of such a configuration that the interdental brush is inserted with the crosspiece from the side, rather than from above, and can then be flipped upwards.

In case the retaining member has a crossshaped slotted arrangement, the interdental brush 40 shown in FIG. 7 can also be introduced transversely to its longitudinal axis. The annular shoulder 42 is then disposed in the transverse slot and acts as a crosspiece for absorbing laxial tensile stresses.

As can be seen from the above description, the locking position is attained, in a preferred embodiment, by the execution of a transverse motion (i.e. perpendicular to the longitudinal axis of the dental brush). It is, of course, likewise within the scope of the invention to provide a connection with locking action in the axial longitudinal direction (compare FIGS. 1–3, FIG. 10).

The retaining member according to this invention can be manufactured in a very simple way. One end of the handle is equipped with a bore extending therethrough, then the bore is divided by crosswise slotting into two aligned bores, and finally one of these bores is provided with a longitudinal slot so that a pincer-like part of the member is produced.

The fastening element of the interdental brush is preferably a plastic injection-molded part. Likewise, the handle with the retaining member can be fashioned as a one-piece article of injection-molded plastic.

The invention also encompasses an entire tooth cleaning set with at least one handle and several, exchangeable dental brushes. The individual dental brushes differ, for example, with respect to hardness. or length of bristles. The bristle properties or other quality features are advantageously identified by color coding on the transition section.

In summation, it can be noted that the invention provides a novel and particularly simple way of fastening interdental brushes to a holder.

I claim:

1. A handle with a retaining member on one end for exchangeably retaining an interdental brush on the handle, the retaining member comprising a bifurcated end having a pair of spaced arms facing each other and cantilevered in the longitudinal direction of the handle from one end of the handle,
    said bifurcated end comprising a means for exchangeably retaining an interdental brush at right angles on the end of the handle,
    one of said arms comprising a pair of spaced apart opposed fingers cantilevered in the longitudinal direction of the handle and constituting a pincer-like member,
    the other arm of said pair of arms connected opposite the pincer-like member, and
    a slot separating said other arm and said pair of spaced fingers,
    whereby the bifurcated end retaining member is integrally formed on the end of said handle.

2. A handle according to claim 1, wherein said other arm comprises a second pair of spaced apart opposed fingers cantilevered in the longitudinal direction of the handle.

3. A handle according to claim 1, wherein said other arm comprises a solid wall portion having an annular outer end portion.

4. A handle according to claim 1, including a longitudinal slot formed between said pair of spaced fingers, and said other arm includes an aperture therethrough extending transversely to said longitudinal direction of said handle, whereby said aperture is in transverse alignment with said longitudinal slot.

5. A combined handle and an interdental brush having a longitudinal element having a rear end, a front end, and a transverse member, said transverse member connected in proximity to the rear end of said longitudinal element, and a wire with bristles thereon connected to the front end of said longitudinal element and in axial alignment therewith, a retaining member on one end of said handle for exchangeably attaching said interdental brush to the end of said handle, comprising a bifurcated end having a pair of spaced arms facing each other and cantilevered in the longitudinal direction of the handle from one end of the handle,
    one of said arms comprising a pair of spaced apart opposed fingers cantilevered in the longitudinal direction of the handle and constituting a pincer-like member,
    the other arm of said pair of arms connected opposite the pincer-like member,
    a slot separating said other arm and said pincer-like member,
    whereby the bifurcated end retaining member is integrally formed on the end of said handle, and
    said longitudinal element engaged between said pincer-like member and extending normal thereto and to the longitudinal direction of the handle, with said transverse member engaged in said slot between said other arm and said pincer-like member.

6. A combined handle and an interdental brush having a plug-like longitudinal element with a transverse shoulder, a retaining member on one end of said handle for exchangeably attaching the longitudinal element of the interdental brush to the end of said handle, comprising a bifurcated end having a pair of spaced arms facing each other and cantilevered in the longitudinal direction of the handle from one end of the handle,
    one of said arms comprising a pair of spaced apart opposed fingers cantilevered in the longitudinal direction of the handle and constituting a pincer-like member,
    the other arm of said pair of arms connected opposite the pincer-like member,
    said other arm includes an aperture therethrough extending transversely to said longitudinal direction of said handle,
    a slot separating said other arm and said pincer-like member, whereby the bifurcated end retaining member is integrally formed on the end of said handle, and
    said longitudinal element engaged in at least one of said aperture of said other arm and in said pincer-like member, and extending normal thereto and to the longitudinal direction of the handle, with said transverse shoulder engaging one of said other arm or said pincer-like member on a side opposite said slot.

7. A combined handle and interdental brush according to claim 6, in which said transverse shoulder of said interdental brush includes a neck portion on an end of said brush, and said plug-like longitudinal element comprises a compressible head on the opposite end of the neck portion from said brush, the neck portion and compressible head of said interdental brush being locked in place in the aperture of said other arm or the pair of spaced fingers on said bifurcated end.

8. A combined handle and interdental brush according to claim 6, in which said longitudinal element is engaged in said aperture of said other arm and in said pincer-like member, and said transverse shoulder engaging one of said other arm or said pincer-like member on a side opposite said slot.

* * * * *